United States Patent [19]

Giaever

[11] 3,960,489

[45] June 1, 1976

[54] METHOD AND APPARATUS FOR DETERMINATION OF CONCENTRATION OF IMMUNOLOGICALLY REACTIVE BIOLOGICAL PARTICLES

[75] Inventor: Ivar Giaever, Schenectady, N.Y.

[73] Assignee: General Electric Company, Schenectady, N.Y.

[22] Filed: Apr. 1, 1974

[21] Appl. No.: 457,092

[52] U.S. Cl. .......................... 23/230 B; 23/253 R; 23/253 TP; 23/259; 195/127; 195/103.5 R; 424/12
[51] Int. Cl.² ........................................ G01N 33/16
[58] Field of Search ............ 23/230 B, 253 R, 259; 424/12; 195/103.5 R, 127

[56] References Cited
UNITED STATES PATENTS

| | | | |
|---|---|---|---|
| 3,389,966 | 6/1968 | Saravis | 424/12 X |
| 3,390,962 | 7/1968 | Goldsmith | 424/12 X |
| 3,645,687 | 2/1972 | Nerenberg | 23/230 B X |
| 3,674,438 | 7/1972 | Shen | 23/230 B X |
| 3,718,436 | 2/1973 | Ushakoff | 23/253 R |
| 3,725,004 | 4/1973 | Johnson | 23/230 B |
| 3,736,100 | 5/1973 | Rains | 23/230 B X |
| 3,770,380 | 11/1973 | Smith | 23/230 B |
| 3,791,930 | 2/1974 | Saxholm | 23/230 B X |
| 3,853,467 | 12/1974 | Giaever | 23/230 B |

*Primary Examiner*—Morris O. Wolk
*Assistant Examiner*—Sidney Marantz
*Attorney, Agent, or Firm*—Leo I. MaLossi; Joseph T. Cohen; Jerome C. Squillaro

[57] ABSTRACT

The area of a bimolecular layer formed on a metallized slide is related to the concentration of second immunologically reactive biological particles forming the second layer. The slide initially has adsorbed thereon a first monomolecular layer of first immunologically reactive biological particles specific to the second particles. A second slide is placed on top of the monomolecular layer coated slide and a moistened region between the two slides is exposed to a solution of the second biological particles to form the second monomolecular layer. The biomolecular layer is visible with good contrast to the unaided eye.

36 Claims, 14 Drawing Figures

METHOD AND APPARATUS FOR DETERMINATION OF CONCENTRATION OF IMMUNOLOGICALLY REACTIVE BIOLOGICAL PARTICLES

My invention relates to a method and apparatus for determining the concentration of immunologically reactive biological particles in a specimen and, in particular, for obtaining the quantitative determination of an antigen-antibody reaction on a solid substrate surface visible to the unaided eye.

This application is related to my concurrently-filed applications Ser. No. 457,093 entitled "Method and Apparatus For Detecting Immunologic Reactions by Diffusion in Gel," Ser. No. 457,094 entitled "Method and Apparatus for Detecting Immunologically Reactive Biological Particles," and Ser. No. 457,091 entitled "Method and Apparatus for Quantitative Surface Inhibition Test," as well as to my copending applications Ser. No. 266,278, "Method and Apparatus for Detection and Purification of Proteins and Antibodies" filed June 26, 1972, now abandoned; Ser. No. 384,113 entitled "Improved Method and Apparatus for Detection and Purification of Proteins and Antibodies" filed July 30, 1973, now abandoned, and Ser. No. 445,204 entitled "Improved Substrate for Immunological Tests and Methods of Fabrication Thereof" filed Feb. 25, 1974, and assigned as herein.

Immunological reactions are highly specific biochemical reactions in which a first immunologically reactive biochemical particle (generally protein) known as the antigen, combines (links) with a second protein specific to the antigen and known as the antibody, to form an immunologically complexed protein. Immunological reactions taking place within a biological system, such as an animal or human being, are vital in combating disease. In a biological system, the entry of a foreign protein, i.e., the antigen, causes the biological system to produce the specific antibody proteins to the antigen in a process not fully understood at this time. The antibody protein molecules have available chemical combining or binding sides which complement those of the antigen molecule so that the antigen and antibody link or bond to form an immunologically complexed protein.

Most antigens are proteins or contain proteins as an essential part, whereas all antibodies are proteins. Proteins are large molecules of high molecular weight, i.e., are polymers consisting of chains of variable numbers of amino acids. The above-cited copending applications disclose that an arbitrary protein will adhere to a substrate in a monomolecular layer only, and that no other arbitrary protein will adhere to the protein layer. On the other hand, the specifically reacting protein to the first protein adsorbed onto the substrate will immunologically bond thereto. In accordance with the teachings of those applications, this discovery is exploited to provide medical diagnostic apparatus in which a slide having a monomolecular layer of one protein adsorbed thereon is used to test suspected solutions for the presence of the specifically reacting protein thereto. If the specifically reacting protein is present in the solution, the slide after exposure to the solution has a bimolecular protein layer thereon. If the specifically reacting protein be absent from the solution, the slide after exposure to the solution has only the original monomolecular layer thereon. Optical, electrical and chemical means for distinguishing between bimolecular and monomolecular biological particle layers are taught in the related copending applications and have different degrees of sensitivity and economy.

Because antibodies are produced by biological systems in response to invasions thereof by foreign proteins, the detection of antibodies in a biological system is of medical diagnostic value in determining the antigens to which the system has been exposed. A typical example of diagnostic detection of antibodies is the detection of antibodies to syphilis or gonorrhea in human serum. Conversely, the detection of certain antigens in a biological system also has medical diagnostic value; examples of diagnostic detection of antigens include detection of HCG protein molecules in urine as a test for pregnancy, and detection of hepatitis-associated-antigen (HAA) molecules in the blood of prospective donors.

In order to perform such diagnostic tests, the appropriate protein of the immunologically reacting pair must be obtained. The only known source of an antibody protein is a living biological system. More particularly, only vertebrates are known at this time to exhibit immunological reactions to the introduction of a foreign protein. For example, many antibodies are found in the blood serum of animals and human beings which have been exposed to the corresponding antigens. Many antigens, however, may be controllably produced in laboratory cultures. However, some antigens, for example hepatitis-associated-antigens, are at present, like antibodies, only obtainable from the higher living biological systems.

It is known in the immunological art that antibody molecules function as antigens when introduced intto the system of a vertebrate to whom they are foreign proteins. Accordingly, specifically reacting antibodies to a given antibody may be readily produced in such vertebrate system.

As presently practiced, both the collection and purification, and the diagnostic utilization of immunologically reactive biological particles rely upon the precipitating or agglutinating characteristic of the proteins resulting from the immunological complexing reaction. The classic example of these diagnostic uses is the blood typing procedure in which blood samples are mixed with serum antibodies and blood type is determined by observing any agglutination occurring in the blood samples.

Another diagnostic utilization of immunologically reactive biological particles is the HCG protein pregnancy test which is currently practiced as an inhibition test. The test is performed by mixing a quantity of anti-HCG serum into a urine specimen. A plurality of polystyrene spheres which have been coated with HCG protein are then introduced into the previously prepared urine specimen. The polystyrene spheres will agglutinate if, but only if, HCG protein is absent from the urine specimen. If HCG protein is absent from the urine specimen, the HCG protein on the polystyrene spheres complexes with the anti-HCG serum previously introduced into the urine specimen and the spheres agglutinate. If, on the other hand, HCG protein is present in the urine specimen, it complexes with the previously introduced anti-HCG serum so that the introduced anti-serum is not available to complex with the HCG protein on the spheres to cause agglutination thereof. Further, in the case of other type protein diagnostic tests such as for the detection of hepatitisassociated antigen, it would also be highly desirable to obtain a more sensitive test and one which would result in a measurement of the concentration of the antibodies or antigens. The shortcoming of agglutination tests is that the particles involved may tend to agglomerate for any of a variety of reasons having nothing to do with immunological agglutination, thereby decreasing the reliability of the test. Typically, agglutination tests are performed with great care by skilled technicians, but occasional diagnostic errors occur.

Although the substrates (slides) described in my herein-above-referenced patent applications are satisfactory in their performance for detecting a bimolecular layer of immunologically reactive biological perticles, such slides do not by themselves indicate the concentration in a solution of the biological particles forming the second monomolecular layer on the substrate unless a timing process is used. That is, the use of the metallized slide alone does not readily provide a means for obtaining a determination of the concentration of the second particles in a specimen such as a blood sample. Another type of metallized slide known in the prior art is the anodized tantalum slide described in the articles "Interactions Among Human Blood Proteins at Interfaces," authors L. Vroman et al., Federation Proceedings, Vol. 30, No. 5 (September–October 1971) pages 1494–1502 and "Three Simple Ways to Detect Antibody-Antigen Complex on Flat Surfaces," authors A. L. Adams et al., Journal of Immunological Methods 3 (1973) pages 227–232, however this anodized tantalum slide is less sensitive than my indium-gold alloy, indium oxide slide disclosed and claimed in by above-referenced copending application Ser. No. 445,204, especially in the detection of hepatitis. Another article related to prior art metallized slides is "Immunologic and Enzymatic Reactions Carried Out at A Solid-Liquid Interface," by Alexandre Rothen, Physiological Chemistry and Physics 5 (1973) pages 243–258.

Therefore, a principal object of my invention is to provide a simple method and apparatus for determining the concentration of immunologically reactive biological particles in a solution suspected of containing such particles.

Another object of my invention is to provide a simple method and apparatus for obtaining by direct visual observation a determination of the concentration of immunologically reactive biological particles which are involved in an immunological reaction occurring at a solid surface.

Briefly, and in accordance with the objects of my invention, I determine the concentration of second immunologically reactive biological particles in a test solution by a direct visual observation of the area of a monomolecular layer thereof formed on a metallized slide. The area of the layer is related to the concentration. First immunologically reactive biological particles are initially adsorbed on the surface of the metallized slide to form a first monomolecular layer thereof. A second member such as a clean glass slide is placed on top of the monomolecular layer coated slide and a drop of water moistens a region between the two slides by capillary action. The moistened region is then exposed to a specimen of the test solution suspected of containing the second biological particles that are specific to the first particles. Presence of the second particles in the test solution forms the second monomolecular layer on top of the first and is visible to the unaided eye with good contrast. The exposure of the moistened region between the two slides to thhe specimen may be accomplished by diffusion of a drop thereof deposited in a hole through the top slide or by depositing such drop on the monomolecular layer coated slide along the edge of the top slide. Alternatively, the second layer is formed more rapidly by a forced flow of the test solution through the hole in the top slide with the solution exiting from the apparatus along the edges of the slides or from the end of a narrow channel formed in the bottom surface of the top slide. Alternatively, the second layer can be rapidly formed electrophoretically by having a pair of electrodes connected to a d.c. voltage supply and positioned at opposite ends of a channel formed in the bottom surface of the top slide so that the biological particles move along the electric field lines. In all cases the concentration of the second particles is related to the size or area of the double layers.

The features of my invention which I desire to protect herein are pointed out with particularity in the appended claims. The inventtion itself, however, both as to its organization and method of operation, together with further objects and advantages thereof, may best be understood by reference to the following description taken in connection with the accompanying schematic drawings wherein:

Figure 1A:
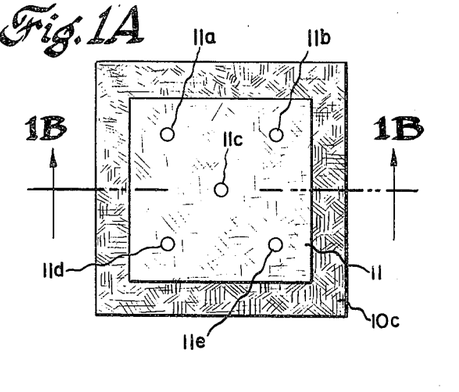
FIG. 1A is a plan view of a first embodiment of the apparatus in accordance with my invention for determining the concentration of immunologically reactive biological particles in a specimen.
Figure 1B:
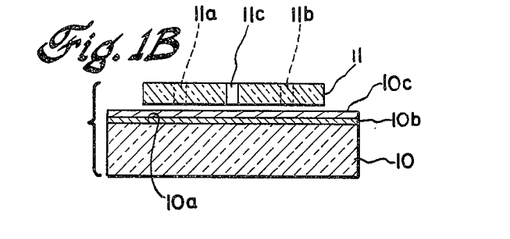
FIG. 1B is an elevation view, in section, of the apparatus illustrated in FIG. 1A taken along line 1B—1B.

Referring now to FIGS. 1A and 1B, there are shown respectively a plan and elevation view of a first and preferred embodiment of an apparatus, in accordance with my invention, for obtaining determination of the concentration of immunologically reactive biological particles in a test solution. The biological particles from the test solution form a second monomolecular layer on a metallized solid substrate after having a first monomolecular layer of immunologically reactive biological particles specific to the particles in the test solution initially adsorbed on the metallized surface of the substrate. The apparatus basically consists of a metallized solid substrate 10 and a second member 11 which is placed on top of substrate 10 as illustrated in FIGS. 1A and 1B. The spacing between substrate 10 and member 11 is exaggerated in FIGS. 1B, 3B and 4B for purposes of indicating the separate components of my apparatus. Substrate 10 has a substantially flat top surface 10a and is fabricated of a suitable material which may be a metal, glass, plastic or similar material. Substrate 10 is preferably in the form of a glass slide such as a conventional microscope cover glass that is readily commercially available. The top flat surface 10a of substrate 10 is metallized in accordance with the teaching disclosed in my above-identified patent applications which are hereby incorporated herein. As examples of such teachings, the metallization may consist of (1) a noncontinuous layer, i.e., metal particles or globules with indium being a typical metal, or (2) a first layer of the indium globules overlayed with a thin gold film or (3) a first layer of the indium globules (or a constant thickness continuous layer of indium) overlayed with a thin film of gold which is alloyed with the indium and a thin oxide film of the indium, or (4) a metal such as nickel and oxide film thereof. The indium particle metallization is often a preferred embodiment of generally equal size first and second biological particles due to the high sensitivity. The noncontinuous layer of indium particle metallization requires use of a light-transmissive substrate material such as glass or plastic, and the indium particles evaporated on the substrate surface have diameters on the order of 1000 Angstrom although the precise size of the particles is not critical as long as they have diameters equal to a large fraction of a wavelength of visible light. The color of the indium particle metallization is a light brown. The color of the indium particle metallization is a light brown. As indicated in my above-referenced application Ser. No. 455,204, the latter indium-gold alloy and indium oxide coated substrate is often a preferred embodiment for two greatly uneven size first and second biological particles since it provides the best contrast, visible to the unaided eye, between single and double monolayers of such immunologically reactive biological particles, a typical example being the hepatitis antigen and antibody. Following the teaching in the above-referenced patent application, the thickness of the indium is approximately twice the thickness of the gold when initially deposited (indium thickness is approximately 2000 A, gold is approximately 1000 A) and the indium oxide film is several hundred Angstrom to obtain a bronze color of such film. As noted in such patent application, the degree of oxidation of the first metal determines the color of the oxidized film so that various degrees of oxidation produce different colored slides having different sensitivities for different thicknesses of the layers of the biological particles.

In the case of the metallized coating 10b on the top surface of substrate 10 being formed of globules of a first metal such as indium, or indium-gold alloy, and the oxide film of indium, the top surface of such metallized coating is slightly irregular. Alternatively, such metallized coating when formed with a continuous, constant thickness layer of the indium, film of gold and the indium oxide, has a top surface substantially flat. Either type of metallized substrate 10 may be utilized in any of the embodiments of my invention depicted herein. The second member 11 may typically be a clean glass slide having dimensions the same as, or different from that of substrate 10. In a typical application, and for convenience in depicting my apparatus, the second member 11 is illustrated in all of the figures as being of smaller length and width dimension than substrate 10. Finally, the second member 11 has one or more holes 11a, 11b, 11c, 11d and 11e formed therethrough. In the case of more than one hole, the holes are spaced from each other, and preferably, although not necessarily, would be symmetrically arranged as indicated for the particular orientation of five holes in FIG. 1A. These holes are of equal small size each having a diameter in the range of a fraction of a millimeter to one centimeter.

Substrate 10 has dimensions in the order of a one inch square or less depending upon the number of holes 11a–e formed in upper slide member 11. Thus, in the case of second member 11 having only a single hole therethrough, substrate 10 may be as small as a half inch square and member 11 may also be a half inch square or smaller. Further details of the substrate metallization and fabrication thereof are disclosed in my above-referenced patent applications which are hereby incorporated by reference herein.

Figure 3A:
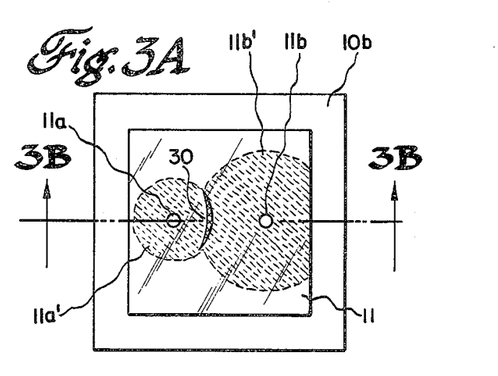
FIG. 3A is a plan view of a second embodiment of my apparatus utilized primarily for detecting the presence of the biological particles but also providing some degree of determination of the concentration thereof.
Figure 3B:
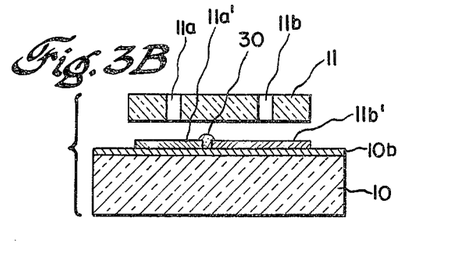
FIG. 3B is an elevation view, in section, of the apparatus illustrated in FIG. 3A along line 3B—3B.

After metallized substrate 10 and top second member 11 have been selected, a monomolecular layer of a first immunologically reactive biological particle is adsorbed onto the coated surface 10b of substrate 10 in all of the embodiments except FIGS. 3A and 3B. The adsorption of the first biological particles may be accomplished by simply immersing the substrate in a solution of the first biological particles so as to completely cover the metallized surface. Alternatively, several drops of the solution may be deposited on the metallized surface and the substrate is maintained in a moist chamber. The first biological particle is selected on the basis of its being specific to particular second immunologically reactive biological particles which will immunologically combine with the first particles to form a smaller second monomolecular layer on the substrate surface if they are present in a solution being tested. The first particles may be produced in laboratory cultures or obtained from the higher living biological systems as described hereinabove, and are commercially available in highly purified form, and if not available commercially, may be purified chemically. The solution of the first biological particles is typically a salt solution of water or other liquid appropriate to, and not reactive with, the first biological particles or a human serum sample. After the substrate has been immersed in the solution for a time interval sufficient so that the first biological particles (and any other nonspecific biological particles that may be present therein) in solution are adsorbed onto the surface of substrate 10 and form a substantially complete monomolecular layer 10c along the entire top surface of the metallized coating 10b in accordance with the teachings of the aforementioned patent applications, the substrate is removed from the solution. The time interval (generally up to one hour) for the formation of the monomolecular layer 10c on substrate 10 is an inverse function of the concentration of the first particles in the solution. A rinsing of the coated surface of substrate 10 is often recommended after the formation of the monomolecular layer 10c thereon in order to remove extraneous matter. The monomolecular layer coated substrate 10 is then dried, preferably by blowing air at room temperature across the substrate in order to speed the drying process. The monomolecular layer 10c on the substrate coated surface has a thickness generally in the range of 30 to 100 Angstrom, which dimension is, of course, determined by the particular biological particle forming such first layer and is visible to the unaided eye as a darker shade of brown on the indium particle slide and is barely, if at all, visible on the indium-gold alloy, indium oxide slide.

After the first monomolecular layer 10c has been adsorbed over substantially the entire top surface of the metallized substrate 10, the second member 11 is positioned on the top surface of the monomolecular layer coated substrate. Although this arrangement of monomolecular layer coated substrate 10 and second member 11 may be satisfactory in some cases wherein the metallized coating 10b on the substrate is formed from the indium globules, it has been found in many such cases that the test solutions deposited into the holes 11a-e form nonreproducible and excessively large size second monomolecular layers by capillary action resulting from the irregular spacing between the bottom surface of second member 11 and the irregular top surface of monomolecular 10c due to the top surface of substrate coating 10b being irregular. Thus, in the case of the irregular surfaced coating 10b on substrate 10, it is preferable to apply a slight clamping force to maintain the bottom surface of second member 11 in greater contact with monomolecular layer 10c on substrate 10 so as to obtain reproducible results. In the case wherein metallized coating 10b is fabricated with constant thickness layers of indium and gold (and indium oxide) such clamping force is not generally required. The clamping, if required, is obtained with any suitable clamping device for clamping together members 10 and 11. The apparatus of all my embodiments may be sold commercially as a device consisting only of metallized substrate 10 and second member 11 or it may also include monomolecular layer 10c.

With the second member 11 positioned (and clamped, if necessary) on the monomolecular layer coated substrate 10, as illustrated in FIGS. 1A and 1B and the other embodiments, the region between the slides 10, 11 to be utilized for the concentration determination is moistened to obtain a subsequent reproducible diffusion of a solution which may include the second biological particles. The moistening step is typically achieved by depositing a drop of water into each of the one or more holes 11a-e to be utilized for testing solutions suspected of containing second immunologically reactive biological particles which are specific to the first particles forming monomolecular layer 10c. The drop of water is drawn in between the bottom surface of second member 11 and the free surface of monomolecular layer 10c by capillary action. The clamping of members 10 and 11, when utilized, also minimizes the amount of water necessary in this moistening step.

The apparatus illustrated in FIGS. 1A and 1B, and the other embodiments, is placed in a moist chamber either just before or just after the inter-slide region is moistened with water. The moist chamber is used to maintain the inter-slide region of interest in the moistened state since subsequent diffusion of a drop of the test solution may take up to several hours and during such interval the moistened region would dry out and thereby prevent the diffusion of the test solution along the monomolecular layer 10c.

After the two-slide apparatus is deposited in the moist chamber and the drop of water has been drawn in between the two slides by capillary action, a drop of a solution to be tested for the presence and concentration of a second immunologically reactive biological particle which is specific to the first particle forming monomolecular layer 10c is deposited into one of the holes 11a-e. In the case of several different test solutions, single drops thereof are deposited in the various holes so that each hole has introduced therein a drop from only one of the solutions. The two-slide assembly is then retained in the moist chamber for a predetermined length of time so that if the second particles are in the test solution, the diffusion of the drop of test solution through the stationary layer of moisture established between the two slides will form a monomolecular layer of the second biological particles due to immunological reaction between the first and second particles. After the predetermined length of time (which may be several hours) has passed, the upper slide 1 is removed and substrate member 10 is rinsed, typically with distilled water, dried, and then visually inspected by observing with the unaided eye the light reflected off or transmitted through the coated surface of substrate 10. In the case of the indium particle slide, light transmission is utilized and for the indium-gold alloy, indium oxide slide, light reflection is utilized in the examination. Absence of the second particles in the test solution results in no second monomolecular layer being formed on top of the first monomolecular layer 10c in the region of the hole in which the drop of test solution was deposited. However, presence of the second particles in the test solution does result in the formation of the second monomolecular layer radially outward along the free surface of monomolecular layer 10c from the region corresponding to the hole in second member 11. The diameter or area of this second layer is related to the concentration of the second biological particles in the test solution. Thus, by measuring the diameter of the second layer, the concentration of the second particles in the test solution can be determined. The diameter of the second layer is, of course, dependent on both the duration of the diffusion step as well as the concentration of the second particles in the test solution. Thus, by establishing a fixed time interval for the diffusion step for all of the measurements, and introducing a drop of solution containing a known concentration of the second particles into one of the holes as a standard, the concentration of the test solutions can be readily determined in one method. Alternatively, the concentration can be estimated merely by observing the area or diameter and comparing it mentally with previous experience. As noted above, any number of different test solutions may be quantitatively evaluated at the same time on the same apparatus by utilizing the other holes for the other test solutions.

Figure 2A:
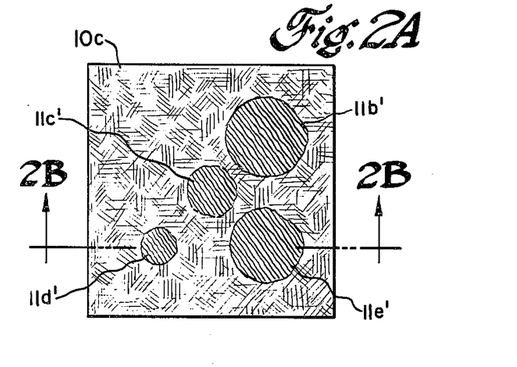
FIG. 2A is a plan view of the metallized slide shown in FIG. 1A after it has been exposed to the specimen and the upper slide removed.
Figure 2B:
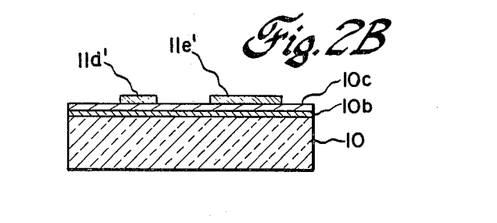
FIG. 2B is an elevation view, in section, of the apparatus illustrated in FIG. 2A along line 2B—2B.

FIG. 2A is a plan view and FIG. 2B an elevation view of the coated surface of substrate 10 upon completion of the quantitative measurement described hereinabove. It is assumed that a drop of the standard solution (i.e., known concentration) has been deposited in the center hole 11c so that the "standard" second monomolecular layer 11c' formed on monomolecular layer 10c under hole 11c is in the center of substrate 10. A drop of a first test solution deposited in hole 11a resulted in the formation of no second layer on the coated surface of substrate 10 underneath hole 11a and therefore such first test solution does not contain any or any significant number of the second particles. A drop of a second test solution deposited in hole 11b resulted in the largest diameter (twice that of layer $11c'$) second layer $11b'$, the diameter measurement indicating a concentration much higher than that of the standard solution by comparison with the diameter of layer $11c'$. A drop of a third test solution deposited in hole $11d$ resulted in a second layer $11d'$ of diameter slightly less than standard layer $11c'$, the measurement indicating the concentration of the third test solution being somewhat less than that of the standard concentration. Finally, a drop of a fourth test solution deposited in hole $11e$ formed a second monomolecular layer $11e'$ having a diameter approximately 1.75 times the standard diameter.

In many cases, the first monomolecular layer $10c$ of biological particles will be of particular antigens such as hepatitis B antigen (BHAg). In such case, the test solutions would be of human serum taken from patients suspected of having had hepatitis B, and in a direct test therefor, the presence and concentration of antibodies to hepatitis B (HBA$b$) would be determined by measuring the diameters of the test and standard second monomolecular layers. Alternatively, the particles in the first monomolecular layer $10c$ can be antibodies to a particular disease, and in a direct test, the presence and concentration of antigens to such antibodies in the serum sample would be determined.

An indirect or inhibition test for the detection and determination of concentration of a particular immunologically reactive biological particle may also be obtained with my apparatus illustrated in any of the figures herein. The principle of the inhibition test is that the first particles, if present in sufficient quantity, will neutralize free second particles in solution. Thus, in the inhibition test, HBAg particles, if present in sufficient quantity, will neutralize free HBA$b$ particles introduced into the solution. This reaction will prevent the antibodies from forming observable complexes, (i.e., a bimolecular layer) when the slide with an antigen layer (first monomolecular layer) is exposed to the test solution.

The inhibition test for an antigen, and specifically HBA$g$ is accomplished as follows: A monomolecular layer $10c$ of HBA$g$ is adsorbed on the coated surface $10b$ of substrate 10 as in the direct test described hereinabove. The test solution is prepared by adding a human serum sample to be tested to a solution of HBA$b$ in a vial or other suitable container. The vial is then stored for a time interval sufficient for the HBA$b$ to complex with HBA$g$ in the human serum sample, if the antigen is present therein. The vial is preferably agitated to increase the rate of complexing. Finally, a drop of the test solution is deposited in one of the holes in second member 11, and after a suitable period of time member 11 is removed and the coated surface of substrate 10 is rinsed, dried and visually examined. The results of this inhibition test are the opposite of the direct test, that is, presence of the HBA$g$ in the human serum sample produces no second monomolecular layer, whereas presence of such layer indicates absence of HBA$g$ in the human serum sample.

The inhibition test for the detection of HBA$b$ is performed similarly to the inhibition test for HBA$g$ with the obvious substitution of the antigen for antibody and antibody for antigen in each of the steps.

In the above hepatitis tests, the HBA$b$ may be obtained from human serum of a patient known to have had hepatitis B, or it may be developed in a goat, rabbit, or other suitable animal by injection thereof with the HBA$g$, waiting a suitable incubation period such as two weeks, and then drawing blood containing the specific antibody from the animal and separating the antibody from the remaining blood particles.

In all of the above tests, the second monomolecular layer spot on the coated surface of substrate 10 is indicated by a purplish colored spot in the case wherein coated substrate 10 is fabricated in accordance with the method described in my hereinabove identified copending patent application Ser. No. 445,204 in a preferred embodiment of coated substrate 100 when the first and second biological particles are of very unequal size. However, as noted in such copending application, other colored backgrounds of the oxide film and other colors of the spot produced by the second monomolecular layer are also possible. In the case of the indium particle slide, preferred when the biological particles are of generally equal size, the second layer spot is a distinctly darker shade of brown.

Referring now to FIGS. 3A and 3B, there is shown a second embodiment of my invention which, as distinguished from all of the other embodiments herein, is directed primarily to the detection of the second immunologically reactive biological particles in a test solution, although it also does provide a general indication of the concentration of the second particles in the test solution. The apparatus in FIGS. 3A and 3B is similar to that illustrated in FIGS. 1A and 1B with the exception that the metallized substrate 10 does not have the free surface of the metallized surface $10b$ covered with a monomolecular layer of first biological particles. Thus, the top surface of coated substrate 10 is merely the free surface of the metallization prior to the test being conducted. Two holes $11a$, $11b$ are shown formed through the second slide member 11 (although this is not a structural limitation) and they are preferably along the center line of slide 11 with each hole being spaced from an opposite slide edge by a distance which can be as great as approximately one-fourth the width of the slide. In actual practice, holes $11a$ and $11b$ are spaced closer together. An advantage of my apparatus is that this hole spacing may be reduced to as little as one millimeter between edges of the holes $11a$, $11b$, and the diffusion time for forming the monomolecular layers to be described hereinafter is thereby significantly reduced. Holes $11a$ and $11b$ are in the same size range as the holes in the first embodiment of my invention.

The method of utilizing my apparatus illustrated in FIGS. 3A and 3B also differs from the method described with reference to the first embodiment illustrated in FIGS. 1A–2B in that it employs the double diffusion process and is as follows:

In the case of a test for the mere detection of the second biological particles in a test solution, a drop of a first solution known to contain the first immunologically reactive biological particles is deposited into hole $11a$ after the region between the two slides in the area around the holes has been moistened as in the first embodiment. Immediately thereafter, a drop of a test solution suspected of containing the second immunologically reactive biological particles which are specific to the first is deposited into hole $11b$. The first particles and any nonspecific biological particles in the drop of the first solution form a first monomolecular layer $11a'$ adsorbed onto the free surface of substrate metallization $10b$ along a circular area having its center at the center of hole $11a$. The drop of test solution which may contain the second biological particles and nonspecific biological particles forms a second monomolecular layer $11b'$ adsorbed onto the free surface of the substrate metallization $10b$ along a circular area having its center at the center of hole $11b$ as depicted in FIGS. 3A and 3B. If there is sufficient concentration of either or both the biological particles in the first and test solutions so that the diffusing first and second particles intersect, there is formed on the substrate metallized surface a precipitate line 30 which becomes clearly visible to the unaided eye, indicating the formation of a complexed protein precipitate line which is a straight or curved line. Precipitate line 30 is adhered to the metallized substrate so that when upper slide 11 is removed, a permanent record of the immunological reaction remains on substrate 10 which is clearly visible without requiring any staining. Assuming equal diffusion rates of the biological particles, the position of the precipitate line 30 between the two holes $11a$ and $11b$ indicates the relative concentration of the biological particles in the two solutions. Thus, as illustrated in FIGS. 3A, 3B, it is assumed that the concentration of the second biological particles in the drop of solution introduced into hole $11b$ is substantially greater than that of the first particles in the solution deposited in hole $11a$ since the intersecting precipitate line 30 is one-third the spacing from hole $11a$. Obviously, if the diffusion rate of the two biological particles is different with equal concentrations thereof, such distinction must be factored into the calculation for determining the concentration of the test solution from the position of precipitate line 30. Again, as in the case of the first embodiment, the drops of the two solutions are allowed to diffuse between the two slides for a predetermined time which in this embodiment is sufficient for the first and second biological particles to intersect and form the precipitate line. Absence of complexed precipitate line 30 indicates either that the test solution does not contain any of the second particles, or that it contains such a low concentration thereof that no significant immunological reaction can occur. It should be noted that this double diffusion technique is related to the prior art Ouchterlony technique which has the disadvantage that staining is required to obtain a permanent precipitate line, and this staining process is a relatively complicated process. In the case where the first solution is known to contain the first biological particles, more than two holes may be formed through member 11, and a convenient arrangement of the holes would be as in FIG. 1A wherein a specimen of the first solution is deposited into the centrally located hole $11e$, and specimens of various test solutions suspected of containing the second biological particles are deposited into the surrounding holes $11a$, $11b$, $11d$, $11e$. In each case of sufficient concentration of the second particles in the corresponding test solution, a precipitate line is formed at the intersection of the diffusing first particles and the corresponding specimens of diffusing second particles, and is a detection test for the presence of the second biological particles in the test solutions. In the case where the first solution is known to contain the first biological particles, and one of the other solutions contains a known concentration of the second particles, a specimen of the first solution is deposited into centrally located hole $11c$ and a specimen of the "standard solution" (known concentration of second particles) is deposited into one of the surrounding holes, say hole $11a$. The relative position of the precipitate line formed between holes $11c$ and $11a$ is then the standard against which the relative positions of any other precipitate lines, formed as the result of specimens of test solutions suspected of containing the second biological particles being deposited in the other surrounding holes $11b$, $11d$, $11e$, are compared in order to determine the concentration of the second particles in such test solutions. In this latter (concentration) test, the surrounding holes are equidistant from central hole $11c$.

Figure 4A:
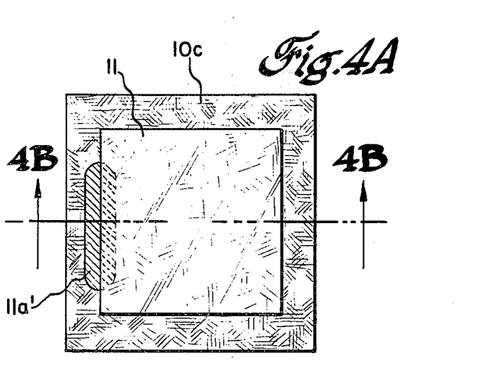
FIG. 4A is a plan view of a third embodiment of my apparatus utilizing diffusion of the specimen.
Figure 4B:
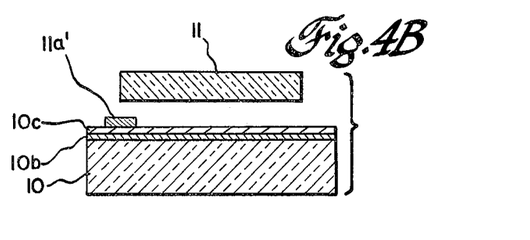
FIG. 4B is a elevation view, in section, of the apparatus illustrated in FIG. 4A along line 4B—4B.

Referring now to FIGS. 4A and 4B, there is shown a third embodiment of my apparatus which is closely related to the apparatus depicted in FIGS. 1A and 1B but operates in a slightly different manner. In particular, substrate 10 is metallized and the monomolecular layer $10c$ of first biological particles is adsorbed thereon as in FIGS. 1A and 1B. The distinction between the structure of the two embodiments is in the fact that the second slide 11 does not have any holes therethrough in my present third embodiment. In the absence of the holes, one or more drops of water are deposited on the monomolecular layer coated surface $10c$ of substrate 10 along one or more edges of slide 11 so that such drop or drops of water are drawn in between the two slides by capillary action in one dimension from such edge (or edges) of the slide. In FIGS. 4A and 4B I show only one of the edges of slide 11 being used. After the particular region(s) between the two slides has been moistened, I deposit one drop (or more than one drop spaced along the edge of slide 11) of the test solution on the monomolecular layer coated surface of substrate 10 at the moistened edge of slide 11 and allow such drop(s) of solution to diffuse for a predetermined length of time between the slides. As indicated in FIGS. 4A and 4B, presence of the second biological particles in the test solution forms a second monomolecular layer $11a'$ in a direction perpendicular to the edge of slide 11 along which the drop was deposited. The width of the second monomolecular layer $11a'$ (as measured between the depicted two long sides thereof) is a measure of the concentration of the second biological particles in the test solution. As in the case of the FIGS. 1A–2B embodiment, a drop of a standard solution (i.e., containing a known concentration of the second biological particles) may be deposited along a second edge of slide 11 for comparison with the test solution if a standard has not already been established at a prior time. Also, it should be evident that the other edges of slide 11 could be utilized for testing the concentration of other test solutions containing, or suspected of containing, the second biological particles.

Figure 5A:
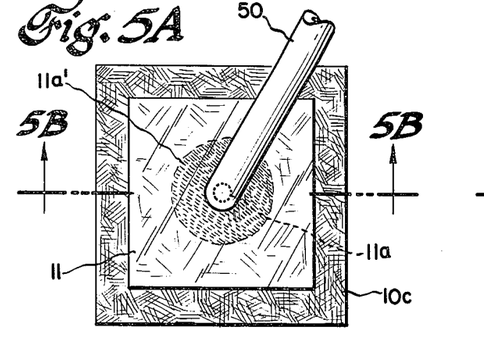
FIG. 5A is a plan view of a fourth embodiment of my apparatus utilizing forced flow of the specimen.
Figure 5B:
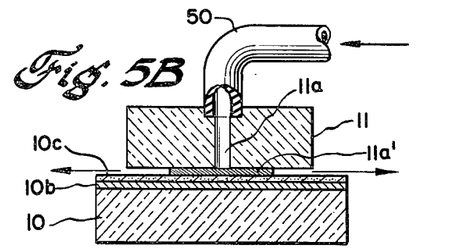
FIG. 5B is a elevation view, in section, of the apparatus depicted in FIG. 5A along line 5B—5B.

Referring now to FIGS. 5A and 5B, there is shown a fourth embodiment of my apparatus for determining the concentration of particular immunologically reactive biological particles in a test solution. In the first three embodiments described hereinabove with reference to FIGS. 1A, 1B, 2A, 2B, 4A, 4B, the second biological particles form the second monomolecular layer as the drop of the test solution diffuses between the two slides. Such process obviously is relatively slow, taking up to 24 hours, and depending on the concentration of the particles in the test dolution. The process of developing the second monomolecular layer can be speeded up by utilizing an effective mechanism such that the second biological particles are more quickly distributed in the region between the slides. A first effective mechanism for increasing this rate of particle distribution is illustrated in the fourth embodiment of my invention in FIGS. 5A and 5B wherein a forced flow of the second solution is utilized by applying pressure to the test solution flowing through hole 11a in upper member 11 and thence in the region between the two slides 10 and 11. This forced flow of the test solution is obtained by utilizing tubing 50 having its input end (not shown) connected to a pressurized source of the test solution and an output end suitably connected at the top end of hole 11a in second member 11. Due to this tubing connection, second member 11 is preferably of greater thickness than in the hereinabove described embodiments of my invention where it can be as thin as desired. In all other respects, the structure illustrated in FIGS. 5A and 5B is the same as that of FIGS. 1A and 1B. Due to the flow of the test solution through tubing 50 and hole 11a, the test solution flows out from between the two slides as indicated by the arrows in FIG. 5B. This forced flow of the test solution results in the second biological particles, if present, to immunologically react with the monomolecular layer 10c of first particles in a much shorter time interval than when utilizing mere diffusion. Thus, the monomolecular layer 11a' of second biological particles from the test solution is formed on the monomolecular layer 10c of first particles in a shorter interval, again being formed radially outward underneath hole 11a. For a constant pressure of the fluid flow, the diameter of the second monomolecular layer 11a is again related to the concentration of the second biological particles in the test solution. Again, as in the other embodiment described herein, the concentration can be determined by comparison with the diameter of a second layer formed from a standard solution on a second slide apparatus, or by means of a second hole in second member 11 spaced sufficiently from hole 11a so that the second monomolecular layers will not intersect.

Figure 6A:
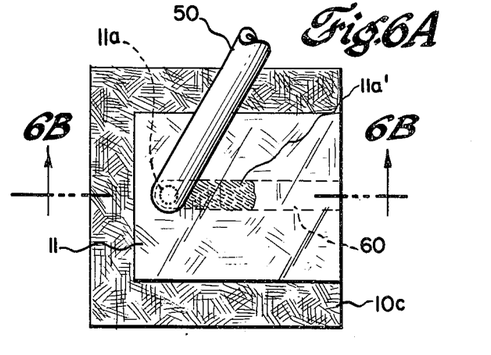
FIG. 6A is a plan view of a fifth embodiment of my apparatus utilizing forced flow.
Figure 6B:
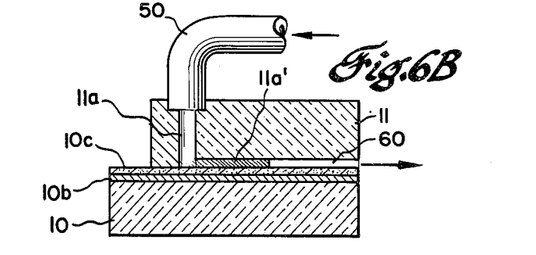
FIG. 6B is an elevation view, in section, of the apparatus illustrated in FIG. 6A along line 6B—6B.

FIGS. 6A and 6B illustrate a fifth embodiment of my apparatus which is very similar to the apparatus illustrated in FIGS. 5A and 5B with the exception that the pressurized fluid flow is contained within a narrow channel 60 between the two slides 10, 11 rather than flowing out in all directions. For this particular embodiment, the metallized coating 10b on substrate 10 is preferably formed from the constant thickness layer of indium in order to obtain a substantially flat top surface of the indium oxide coating as opposed to the irregular surface when utilizing indium globules. Channel 60 may be in the order of 5 micron high and is formed within the bottom surface of second member 11 from the output end of hole 11a to the most distance spaced edge of member 11. Channel 60 has a width equal to or somewhat greater than the diameter of hole 11a so that the pressurized fluid may readily flow through the channel and exit therefrom between the two members as indicated by the arrow in FIG. 6B. The length of the second monomolecular layer 11a' formed within channel 60 on the first monomolecular layer 10c again is related to the concentration of the second biological particles in the solution flowing through tubing 50, hole 11a and channel 60.

A second effective mechanism for speeding up the process of forming the second monomolecular layer of biological particles is the application of an electric field to such particles to thereby speed up the process electrophoretically. FIGS. 7A and 7B illustrate my apparatus which uses the electrophoretic process for speeding up the formation of the second monomolecular layer 11*a'*. The apparatus is similar to the apparatus of FIGS. 6A, 6B with the exception that a narrow channel 70 is formed in the undersurface of second member 11 which extends from the output end of hole 11*a* toward the far edge of second member 11 and no tubing 50 is required. In order to obtain a channel of sufficient length in the FIGS. 6A, 6B, and 7A, 7B embodiments of my apparatus, the hole 11*a* through upper member 11 is preferably formed near the edge of member 11 opposite the edge containing the output end of the narrow channel. In the case of the FIGS. 7A, 7B embodiment, the output end of channel 70 is enclosed by a first electrode 71 which is suitably connected by means of an electrical conductor to a first polarity output of a d.c. voltage supply. In like manner, the end of channel 70 at the output end of hole 11*a* is enclosed by a second electrode 72 connected by means of a second conductor to the opposite polarity output of the voltage supply. The apparatus of FIGS. 7A and 7B is utilized in the following manner: A drop of the test solution suspected of containing the second biological particles is deposited into hole 11*a* and the d.c. voltage supply is energized to provide a suitable d.c. electric field between electrodes 71 and 72. Choice of the proper polarity and magnitude of the voltage applied to the electrodes forces the particular second biological particles to move along the electric field lines with a velocity given by the product of the electrophoretic mobility and the field amplitude. The velocity of the second biological particles therefore also substantially decreases the time interval required for forming the second monomolecular layer on top of the first layer. Again, as in the case of the FIGS. 6A and 6B embodiment, the second monomolecular layer 11*a'* has a length in the axial direction of channel 70 which is related to the concentration of the second biological particles in the test solution.

From the foregoing description, it can be appreciated that my invention makes available a method and apparatus for obtaining a determination of the concentration of a particular immunologically reactive biological particle in a test solution by measuring the size of a second monomolecular layer of the particular particle which is formed on a metallized substrate. The size of the second monomolecular layer is measured from a direct visual observation with the unaided eye and the second monomolecular layer can be formed by a mere diffusion of the solution thereof, or can be more rapidly formed by an effective mechanism such as utilizing a forced flow thereof, or application of an electric field in an electrophoretic process. The size of the second monomolecular layer can be compared to a known standard or a table or graph prepared from the results of tests with standard solutions of known concentrations. As a result, I have provided a simple method wherein the previously described metallized slides described in the hereinabove referenced patent applications can now be adapted to be used for determination of the concentration of biological particles in test solutions. Since the metallized slides can be fabricated repetitively with identical characteristics, the results of the quantitative measurements obtained in accordance with my present invention are very accurate and can serve may useful purposes, especially in the medical diagnostic fields in the analysis of human serum, for example, for the detection and determination of concentration of various antibodies and antigens therein. Since the visual contrast between the single and double layers of immunologically reactive biological particles is very distinct when utilizing my metallized slide, the measurement of the concentration of the second biological particles is accomplished by direct observation with the unaided eye and therefore does not require elaborate test equipment.

Figure 7A:
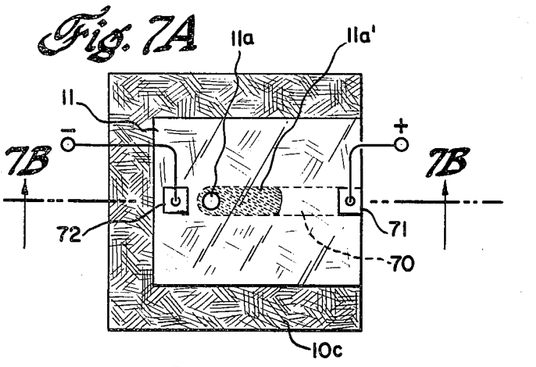
FIG. 7A is a plan view of a sixth embodiment of my apparatus uutilizing electrophoresis.
Figure 7B:
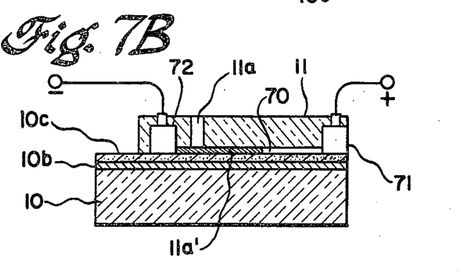
FIG. 7B is an elevation view, in section, of the apparatus illustrated in FIG. 7A along line 7B—7B.

Having described my invention with reference to six particular embodiments, it is believed obvious that modification and variation of my invention is possible in the light of the above teachings. Thus, the shape and size of the various substrates and upper members may be varied and virtually any pair of immunologically reactive biological particles which will immunologically react with each other can be utilized with my apparatus. That is, the biological particles referred to hereinabove as first and second particles may be antigens, antibodies, viruses, bacteria, hormones, enzymes and other particles which can be readily grown or otherwise isolated and collected or are present in human serum or other solution being tested. Also, various metallizations other than those specifically mentioned hereinabove may be utilized and may have superior sensitivity to particular biological particles, as one example the metal-metal oxide metallization may be of nickel. Also, it should be evident that at least some of the embodiments of my invention, namely the FIGS. 1A, 1B, 3A, 3B and 7A, 7B embodiments, may be fabricated without the second member 11 by forming the holes 11a — through the bottom surface of substrate 10 (as oriented in FIGS. 1B, 3B, 7B). The slide would then be turned over and the water and test solution sequentially deposited into the hole(s) to obtain the moistening and subsequent diffusion of second biological particles along the first monomolecular layer. Finally, it should be evident that the second member 11 need not be fabricated of a liquid nonpermeable material. Thus, in place of a rigid, nonpermeable element for member 11 a cellulose membrane or a layer of gel such as agar or agarose may be employed. In the case of member 11 being a cellulose membrane, such membrane is moistened with distilled water (to supply the diffusion medium) and placed in contact with the monomolecular layer 10c coated substrate 10. The need for holes for access to the diffusion medium would be obviated, the specimen of the test solution being deposited on a first selected area of the moist membrane 11. Diffusion of such specimen results in an immunologic reaction whereby a monomolecular layer of the second biological particles is formed on top of the first biological particle layer in the shape of a small circular spot if the test solution contains such second particles. The diameter of the second layer spot, which is visible with good contrast to the unaided eye as a purplish spot in the case of a bronze color metallized slide, is again related to the concentration of the second particles in the test solution. Thus, in FIGS. 1A and 1B, the member 11 as shown may be replaced by a moist cellulose membrane, in which case the circles 11a–e are intended represent drops of various test solutions and perhaps a standard solution of the second particles. In like manner, the member 11 as shown may be replaced by a thin layer of gel solidified on the monomolecular layer coated substrate in which case the circles 11a–e are intended to represent wells in the gel for receiving the specimens which subsequently diffuse through the gel and again form the circular spot of second particles as described above. Thus, my apparatus as fabricated may also consist of metallized substrate 10 with a monomolecular layer 10c of particular first immunologically reactive biological particles adhered thereon, and a second member in place of the rigid nonpermeable member 11 shown which may be a cellulose membrane or layer of gel. After formation of the second layer spot(s), the membrane or gel is removed, the metallized slide is rinsed, dried, and then visually examined with the unaided eye and the diameters of the second layer spots 11b'–e' are measured as before for determining the particle concentration. It is, therefore, to be understood that changes may be made in a particular embodiment of my invention as described which are within the full intended scope of the invention as defined by the following claims.

What I claim as new and desire to secure by Letters Patent of the United States is:

1. Apparatus for determining the presence or absence of select biological particles in a biological sample and the concentration of said select biological particles, if present, comprising in combination
   a solid substrate member having metallized surface area,
   a first monomolecular layer of biological particles immunologically specific to said select biological particles adsorbed on said metallized surface area and
   means for locating a stationary region of an aqueous liquid on and in contact with said first monomolecular layer.

2. The apparatus set forth in claim 1 wherein the metallized surface area of the substrate member is a non-continuous film consisting of metal particles.

3. The apparatus set forth in claim 1 wherein the metallized surface area of the substrate member is formed from an alloy of two metals.

4. The apparatus set forth in claim 1 wherein the first monomolecular layer of first biological particles is adsorbed along substantially the entire metallized surface area of the substrate member.

5. The apparatus set forth in claim 1 wherein the first layer of biological particles are a particular antigen.

6. The apparatus set forth in claim 1 wherein the first layer of biological particles are a particular antibody.

7. The apparatus recited in claim 1 wherein the locating means is a moistened cellulose membrane.

8. The apparatus recited in claim 1 wherein the locating means is a layer of gel having at least one well therein.

9. The apparatus recited in claim 1 wherein the metallized surface area contains oxide of a metal in said metallized surface area.

10. The apparatus recited in claim 1 wherein the metallized surface area is substantially flat.

11. The apparatus set forth in claim 1 wherein the metallized surface area of the substrate member is formed from an alloy of two metals and has an outer oxide film of one of the two metals.

12. The apparatus set forth in claim 11 wherein the two metals are indium and gold and the oxide film is an indium oxide film.

13. The apparatus recited in claim 1 wherein the locating means is a rigid, nonpermeable member disposed in juxtaposition with the first monomolecular layer and close enough thereto to define a passage able to function as a capillary for an aqueous liquid.

14. The apparatus recited in claim 13 wherein the rigid member has at least one aperture therethrough in flow communication with the passage.

15. The apparatus set forth in claim 14 wherein the size of the aperture through the rigid member is of diameter in the range of 1 millimeter to 1 centimeter.

16. A method for determining the presence or absence of select biological particles in a biological sample and the concentration of said select biological particles, if present, comprising the steps of:
depositing a first monomolecular layer of biological particles immunologically specific to said select biological particles on a metallized surface,
disposing a stationary region of moisture on and in contact with said first monomolecular layer,
placing a quantity of biological sample in contact with said stationary region,
maintaining said stationary region to permit diffusion of said quantity of biological sample therethrough into contact with said first monomolecular layer,
removing said stationary region and
inspecting the exposed surface to determine the presence and area of second monomolecular layer adhered to said first monomolecular layer.

17. The method recited in claim 16 wherein the stationary region is in a moistened cellulose membrane placed in contact with the first monomolecular layer.

18. The method recited in claim 16 wherein the stationary region is in a layer of gel placed in contact with the first monomolecular layer.

19. The method recited in claim 16 wherein the first monomolecular layer is a layer of protein.

20. The method recited in claim 16 wherein the metallized surface is irregular.

21. The method recited in claim 16 wherein the metallized surface is substantially flat.

22. The method recited in claim 16 wherein the maintaining of the stationary region is accomplished by providing a moist environment during the diffusion.

23. The method recited in claim 16 wherein a plurality of quantities of biological samples are placed in contact with the stationary region at spaced locations.

24. The method recited in claim 23 wherein a quantity of a standard solution containing a known concentration of select biological particles therein is also placed in contact with the stationary region to produce a standard area of second monomolecular layer.

25. The method recited in claim 16 wherein the stationary region is disposed by capillary action between the first monomolecular layer and surface area of a rigid, nonpermeable member in juxtaposition therewith.

26. The method recited in claim 25 wherein the quantity of biological sample is placed in contact with the stationary region along an edge of the rigid member.

27. The method recited in claim 25 wherein the quantity of biological sample is placed in contact with the stationary region via an aperture through the rigid member.

28. The method recited in claim 27 wherein the quantity of biological sample is placed in contact with the stationary region under pressure.

29. The method recited in claim 27 wherein the quantity of biological sample is placed in contact with the stationary region and simultaneously subjected to a direct current electric field.

30. A method for determining the presence or absence of select biological particles in a biological sample, comprising the steps of:
disposing a stationary region of moisture on a metallized surface in direct contact therewith,
placing a quantity of solution containing biological particles immunologically specific to said select biological particles in contact with said stationary region at a first location,
placing a quantity of biological sample in contact with said stationary region at a second location spaced from said first location,
maintaining said stationary region to permit diffusion of said quantities of solution and biological sample therethrough to contact said metallized surface,
removing said stationary region and
inspecting the exposed surface to determine the presence or absence of precipitate line adhered to said metallized surface between positions thereon in juxtaposition with said first and second locations.

31. The method recited in claim 30 wherein the select biological particle is an antigen and the biological particle specific thereto is an antibody.

32. The method recited in claim 30 wherein the metallized surface contains oxide of a metal in said metallized surface.

33. The method recited in claim 30 wherein the metallized surface is irregular.

34. The method recited in claim 30 wherein the metallized surface is substantially flat.

35. The method recited in claim 30 wherein the stationary region is disposed by capillary action between the metalized surface and surface area of a rigid, nonpermeable member in juxtaposition therewith.

36. The method recited in claim 35 wherein the quantities of solution and biological sample are placed in contact with the stationary region via spaced apertures through the rigid member.

* * * * *